United States Patent [19]

Szycher et al.

[11] Patent Number: 4,727,868

[45] Date of Patent: Mar. 1, 1988

[54] ANISOTROPIC WOUND DRESSING

[75] Inventors: Michael Szycher, Lynnfield; Jonathan L. Rolfe, North Easton, both of Mass.

[73] Assignee: Thermedics, Inc., Woburn, Mass.

[21] Appl. No.: 54,112

[22] Filed: May 20, 1987

Related U.S. Application Data

[63] Continuation of Ser. No. 726,809, Apr. 25, 1985, abandoned, which is a continuation-in-part of Ser. No. 670,810, Nov. 13, 1984, Pat. No. 4,614,787.

[51] Int. Cl.$^4$ .................. C08G 18/10; A61F 13/00
[52] U.S. Cl. ..................... 128/156; 604/304; 604/372; 424/402; 528/75; 66/169 R; 66/193
[58] Field of Search ............... 128/156; 604/304, 372; 424/16; 528/75; 66/169 R, 193

[56] References Cited

U.S. PATENT DOCUMENTS

| | | | |
|---|---|---|---|
| 3,062,210 | 11/1962 | Scholl | 128/156 |
| 3,342,183 | 9/1967 | Edenbaum | 128/268 |
| 3,374,134 | 3/1968 | Waldman | 156/239 |
| 3,526,224 | 9/1970 | Potts | 128/156 |
| 3,567,119 | 3/1971 | Wilbert et al. | 239/6 |
| 3,570,482 | 3/1971 | Emoto et al. | 128/156 |
| 3,598,122 | 8/1971 | Zaffaroni | 128/268 |
| 3,598,123 | 8/1971 | Zaffaroni | 128/268 |
| 3,731,683 | 5/1973 | Zaffaroni | 128/268 |
| 3,734,097 | 5/1973 | Zaffaroni | 128/268 |
| 3,742,951 | 7/1973 | Zaffaroni | 128/268 |
| 3,842,832 | 10/1974 | Wideman et al. | 128/169 |
| 3,870,593 | 3/1975 | Elton et al. | 161/159 |
| 3,881,473 | 5/1975 | Corvi et al. | 128/90 |
| 3,949,742 | 4/1986 | Nowakowski | 128/155 |
| 3,975,567 | 8/1976 | Lock | 428/315 |
| 4,034,751 | 7/1977 | Hung | 128/156 |
| 4,038,239 | 7/1977 | Coyner et al. | 528/75 |
| 4,051,848 | 10/1977 | Levine | 128/156 |
| 4,144,317 | 3/1979 | Higuchi et al. | 424/21 |
| 4,156,067 | 5/1979 | Gould | 528/73 |
| 4,189,467 | 2/1980 | von Bittera et al. | 424/14 |
| 4,209,605 | 1/1980 | Hoy et al. | 528/54 |
| 4,215,684 | 8/1980 | Westip | 128/156 |
| 4,233,969 | 11/1980 | Lock et al. | 128/156 |
| 4,236,550 | 12/1980 | Braun et al. | 139/421 |
| 4,264,757 | 4/1981 | Park | 528/75 |
| 4,306,551 | 12/1981 | Hymes et al. | 128/156 |
| 4,307,717 | 12/1981 | Hymes et al. | 128/156 |
| 4,321,117 | 3/1982 | Kaetsu et al. | 521/28 |
| 4,331,135 | 5/1982 | Westip | 128/156 |
| 4,336,243 | 6/1982 | Sanvordeker | 424/28 |
| 4,340,043 | 7/1982 | Seymour | 128/132 |
| 4,391,106 | 7/1983 | Schafer et al. | 66/193 |
| 4,411,754 | 10/1983 | Kaetsu et al. | 522/20 |
| 4,447,590 | 3/1984 | Szycher | 528/76 |
| 4,460,369 | 7/1984 | Seymour | 604/897 |
| 4,476,697 | 10/1984 | Schafer et al. | 66/193 |
| 4,483,759 | 11/1984 | Szycher et al. | 528/76 |
| 4,496,535 | 1/1985 | Gould et al. | 424/19 |

FOREIGN PATENT DOCUMENTS

| | | |
|---|---|---|
| 273966 | 10/1962 | Australia . |
| 0114581 | 8/1984 | European Pat. Off. . |
| 1476894 | 6/1977 | United Kingdom . |
| 2093702 | 9/1982 | United Kingdom . |

*Primary Examiner*—Delbert R. Phillips
*Assistant Examiner*—Nathan M. Nutter
*Attorney, Agent, or Firm*—Lorusso & Loud

[57] ABSTRACT

An anisotropic wound dressing comprised of a knitted reinforcing fabric which is sandwiched between a crosslinked aliphatic polyurethane. The wound dressing is fabricated by dipping the fabric into a polyurethane-forming coating solution to form a thin film which coates the fibres of the fabric and fills the interstices with a film or layer. The film which coats the fabric is cured by ultraviolet radiation and one side of the film is coated with pressure sensitive adhesive to form a wound dressing. In the most preferred embodiments, the knitted reinforcing fabric is an anisotropic fabric formed with a basic stitch construction to create equally spaced and sized hexagonal interstices. Because of the fabric reinforcement, the resulting oxygen permeable product can be made thin, and yet be anisotropic and strong. The resulting product does not wrinkle easily and holds its shape so it is also easily applied.

30 Claims, 3 Drawing Figures

ANISOTROPIC WOUND DRESSING

CROSS-REFERENCE TO A RELATED APPLICATION

This is a continuation of co-pending application Ser. No. 726,809 filed on Apr. 25, 1985, now abandoned, which is a continuation-in-part of prior application Ser. No. 670,810, filed Nov. 13, 1984, entitled "Drug Dispensing Wound Dressing" and now U.S. Pat. No. 4,614,787.

BACKGROUND OF THE INVENTION

There has long been a need for a wound dressing which is thin, soft, pliable, elastic, oxygen permeable, yet high in tensile strength and abrasion resistance and which does not promote the growth of bacteria.

Presently available bandages made of materials such as cotton are undesirable because they retain water, serve as growth mediums for bacteria, and soak up tissue pieces and blood which clots, causing adhesion to the wound and trauma during removal.

Bandages made of plastic materials to decrease the undesirable water absorption of cotton wound dressings are available. Unfortunately, problems due to the lack of oxygen transmission through the plastic result from the use of many plastic materials. Indeed, holes are punched through the plastic covering to allow the transmission of some oxygen to the skin below. Such constructions do not provide a barrier to low surface tension aqueous solutions, e.g. washing-up liquid (which will also allow bacteria to penetrate). Silicone coatings have been applied to the area of the bandage adjacent to the wound to prevent adhesion. These coatings do not significantly decrease the problem of the bandage sticking to the wound, and do nothing to reduce the blocked oxygen problems.

In further attempts to overcome the adhesion and permeability problems, polyurethane and other plastic dressings were tried. For example U.S. Pat. No. 3,975,567 to Lock discloses a pressure and heat-treated polyurethane foam which is lyophilic and U.S. Pat. No. 3,870,593 to Elton et al. discloses a polymeric film comprised of finely divided particles of non-hygroscopic inorganic salt dispersed in a suitable polymer.

Other polyurethanes which polymerize upon exposure to ultraviolet light were also developed. The majority of these UV-curable polyurethanes were designed for use as orthopedic casts, for example, U.S. Pat. No. 4,209,605 discloses such a cast. None of these compositions managed to combine the properties of softness, oxygen and water vapor permeability, flexibility, and thioxtropy.

The desired material for use as a wound dressing or bandage must be permeable to water vapor, but not permeable to liquid water, microorganisms and particles of dirt. The material should be anisotropic. By anisotropic is meant that the fabric stretches more in one direction than in the other. This characteristic allows the dressing to stretch in the direction of the skin to which it is applied and also allows for easy application.

The material should also be thin so that the dressing is not easily bumped or displaced by contact with outside sources. Other bandages which use a knitted fabric result in a very voluminous bandage. See, for example, U.S. Pat. No. 4,236,550 to Braun et al. and U.S. Pat. No. 4,391,106 to Schafer et al. Thinner wound dressings presently available of polyurethane often require two or more trained medical personnel for proper application because of its thinness, elasticity and tendency to stick to itself during application.

SUMMARY OF THE INVENTION

The present invention is a wound dressing formed of an ultrathin polyurethane membrane which allows light and oxygen to reach the wound while serving as a barrier to bacteria. The wound dressing includes a textile reinforcement fabric within a layer of crosslinked aliphatic polyurethane material. The fabric enables the wound dressing to be made very thin and yet be strong and anisotropic.

It is therefore an object of the present invention to provide a wound dressing which is strong, yet flexible, and which can be made to conform to the shape of the site of the wound.

It is still a further object of the present invention to provide such a material for use as a wound dressing which is anisotropic and thin.

It is still a further object of the present invention to provide a material which can be easily formed and has sufficient support that it retains its shape so that it can easily be applied to a wound by one person in adverse circumstances.

The foregoing and other objects and features of the claimed invention will be understood by those skilled in the art from a reading of the description which follows.

DESCRIPTION OF THE PREFERRED EMBODIMENTS

A wound dressing in preferred embodiment consists of an open mesh knitted fabric which is embedded in a crosslinked aliphatic polyurethane. The polyurethane-forming solution is applied to the fabric as a film, occluding the interstices of the fabric. The polyurethane is then cured by exposure to ultraviolet light. One side of the fabric coated with cured polyurethane may optionally be provided with a pressure sensitive adhesive.

The open mesh knitted fabric is used as a reinforcement. The term "knitted" is intended to describe the process to form textile material by interlacing yarn or threads in a series of connected loops with needles. The reinforcing fabric can be made out of any textile material, such as a polyester. Polyester, however, is considered to be very expensive. A very porous fabric, which is less expensive than a polyester, is the preferred knit fabric. A desirable fabric is a warp knit 15 denier nylon tricot, heat set material. One such fabric is sold by Gehrring Textiles, New York, N.Y., and is formed from Nylon 6-6 yarns. Any fabric of the proper geometry, however, which is biocompatible may be used.

The preferred knitted fabric has the following characteristics. The openings in the fabric are hexagonal, of a size ranging from 0.5 mm to 4 mm across, although preferably they are 2 mm in size. The fabric is knitted from yarns having a diameter in the range of 0.025–0.203 mm, although preferably with a diameter of 0.1 mm. The term "yarn" as used herein is intended to describe both yarns formed from fibers or filaments twisted together and yarns formed from monofilament fibers. The yarn itself need only have modest elongation properties. The stretch characteristics of the fabric is achieved by the mechanical processing and geometry.

Figure 3:
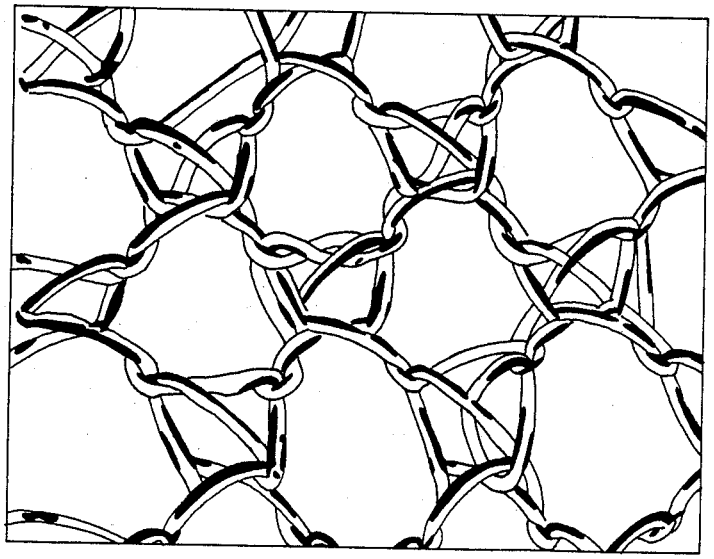
FIG. 3 is a view of the weave of the reinforcing fabric structure of the anisotropic wound dressing of the present invention, magnified 50 times.

The fabric described above is shown in FIG. 3, magnified 50 times. The small thread to large open space ratio is considered important because it minimizes the obstruction of light and moisture, it provides high tear characteristics, suppleness and contributes to the anisotropic tendencies. In its preferred embodiment, the ratio of the diameter of the thread to the size of the void area is 0.1:2, or 5% thread to 95% void area.

An aliphatic polyurethane solution is then applied to the fabric. Any non-thermoplastic aliphatic polyurethane that is bio-compatible is suitable, although one which is also drug dispensing is especially preferred. The preferred formation is the reaction product of isophorone diisocyanate and a macroglycol which results in an isocyanate terminated prepolymer. The prepolymer is then reacted with a chain terminator to form a vinyl terminated polyurethane oligomer. Optionally, a photosensitizer may be admixed with the foregoing compounds at any point prior to curing to form a homogeneous admixture, which is applied to the fabric.

The isophorone diisocyanate (IPDI) used in the present invention is an aliphatic compounds having the following formula:

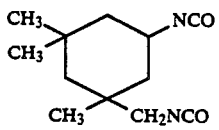

IPDI is utilized in the present invention because it is a liquid at room temperature and thus, easily coats the fabric, and because it cures to a crystal clear product upon exposure to ultraviolet light, rather than yellowing as is the case with many prior art diisocyanates, and because it cures without any temperature rise.

The macroglycol preferred for use in the present invention is a polypropylene glycol (PPG), preferably having a molecular weight of 500–5000 Daltons and, more preferably 1000–3000 Daltons. PPG is preferred because it reacts with the IPDI at a fast rate at room temperature with no temperature rise. Other high molecular weight glycols such as polyethylene glycol (PEG) may be employed, but PEG is a solid at room temperature and a feasible rate of reaction would require heating. As used herein, the term "macroglycol" has reference to any glycol having a molecular weight in excess of 500 Daltons.

The chain terminator used in formulating the products of the invention should have both hydroxyl and vinyl functional groups and is preferably an acrylic compound such as hydroxyethyl acrylate or hydroxyethyl methacrylate. Hydroxyethyl methacrylate (HEMA) is most preferred for use as the chain terminator.

The present invention may be used with or without a drug dispensing polyurethane. Should the drug dispensing characteristics be desired in the final product, a large variety of drugs, including heat labile drugs, may be incorporated into the compositions by the present invention at any point in the formulation/reaction sequence because the process referenced above does not involve an exothermic reaction.

Photosensitizers useful herein include benzophenone, acetophenone, azobenzene, acenaphthenequinone, o-methoxy benzophenone, thioxanthen-9-one, xanthen-9-one, 7-H-Benz(de)anthracen-7-one, 1-naphthaldehyde 4,4'-bis(dimethylamino)benzophenone, fluorene-9-one, 1'-acetonaphthone, 2'-acetonaphthone, anthraquinone, 2-tern.-butyl anthraquinone, 4-morpholino-benzophenone, p-diacetylbenzene, 4-aminobenzophenone, 4'-methoxyacetophenone, diethoxyacetophenone, benzaldehyde, and the like.

Specifically useful herein are acetophenone photosensitizers of the structure:

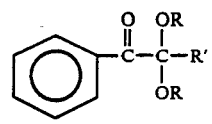

wherein R is alkyl from 1 to about 8 carbon atoms, or aryl of 6 ring carbon atoms and R' is hydrogen, alkyl of from 2 to about 8 carbon atoms, aryl of from 6–14 carbon atoms, or cyclo alkyl of 5 to 8 ring carbon atoms.

Diethoxyacetophenone is the preferred photosensitizer.

The diisocyanate, macroglycol and chain terminator are reacted in approximately stoichiometric amounts, i.e., in the approximate ratio of 2 moles (2.0 equiv.) isophorone diisocyanate to 1 mole (1.0 equiv.) macroglycol to 2 moles (1.0 equiv.) chain terminator. At the end of the reaction between the prepolymer and the chain terminator free isocyanate is monitored by infrared spectrophotometry and, if necessary, additional small amounts of the chain terminator may be added to scavenge any remaining isocyanate. It is important that the low molecular weight monomers present in the composition be reacted prior to contact with the skin so that only compounds with molecular weights of 1500–5000 Daltons are present. The high molecular weight compounds do not leach out of the wound dressing into the underlying tissue and are therefore non-toxic.

An antioxidant such as tetrakis(methylene(3,5-di-tert-butyl-4-hydroxyhydrocinnamate)) may be added to inhibit spontaneous oxygen-initiated curing.

A polyurethane catalyst such as dioctyl tin dilaurate, N-methyl morpholine, trimethylamine, triethylamine, zinc octoate, or dibutyl tin dilaurate is added to both the reaction medium in which the prepolymer is formed and the reaction medium in which the prepolymer is reacted with the chain terminator.

The above polyurethane solution is applied to the fabric described above. This coating step is preferably done by dipping the fabric in the polyurethane solution. The polyurethane coats the fabric fibers and fills the interstices. The thickness of the polyurethane membrane or film sandwiching the fabric is 0.0254 mm or less and preferably is 0.01 mm.

Curing may be accomplished by ultraviolet radiation, typically between 219 and 425 nm for 20 seconds at 0.5 W/cm$^2$. Curing transforms the liquid oligomer into a solid elastomer.

It should be understood that in addition to curing an oligomer, it is also possible to utilize a cured polymer in solution followed by evaporating the solvent while the polyurethane is held by the reinforcing fabric. The two foregoing systems are referred to as "polyurethane-forming solutions".

The fabric coated with cured polyurethane is clear, soft and elastic. The resulting product is also thin, oxygen permeable, anisotropic, strong, does not wrinkle, and therefore, keeps its shape. Because there is no gauze, bacteria buildup is prevented.

Any pressure sensitive adhesive conventionally used for wound dressings or bandages may be spread over one surface of the fabric coated with cured polyurethane, e.g. a polyacrylate adhesive or a polyvinylethyl ether blend adhesive. A release paper or plastic film is then applied over the exposed surface of the adhesive.

Figure 1:
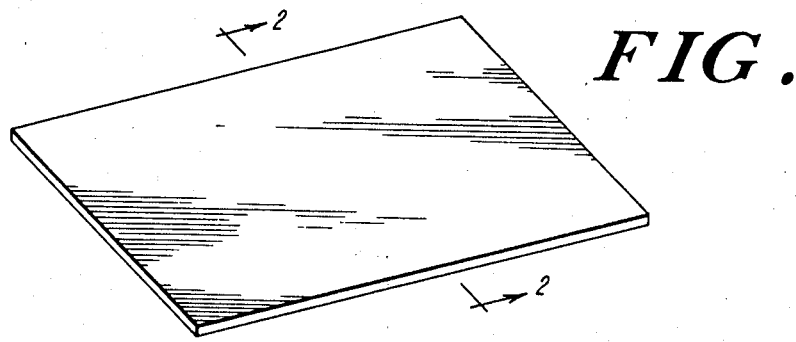
FIG. 1 is a view of the anisotropic wound dressing of the present invention which had been made into a pressure sensitive, self-adhesive first aid dressing.
Figure 2:
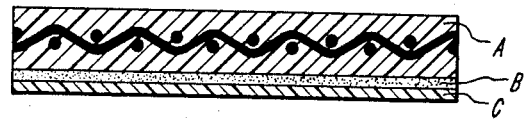
FIG. 2 is a cross-sectional view of the dressing in FIG. 1, taken along the cut at line 2—2, exposing the layers of the dressing.

FIG. 2 is the cross-sectional view of a first aid dressing made from the anisotropic wound dressing of the present invention. The cross-sectional view exposes the various layers of the dressing: A is the coated knitted reinforcing fabric, B is the pressure sensitive adhesive and C is the release paper or plastic film.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing despcription, and all changes which come within the meaning and range of equivalency of the claims are therefore intended to be embraced therein.

What is claimed is:

1. An anisotropic wound dressing comprising a polyurethane encapsulated fabric layer comprising:
   a crosslinked non-thermoplastic polyurethane; and
   a knitted reinforcing anisotropic fabric defining a network of interstices having a void area between the range of 0.5 mm to 4 mm across and formed from yarns having a diameter in the range of 0.025 to 0.203 mm embedded in and encapsulated by said polyurethane; wherein the thickness of the polyurethane in the area of the wound dressing where the polyurethane fills the interstices of said knitted reinforcing fabric is 0.0254 mm or less.

2. The wound dressing of claim 1 wherein said void area of said knitted reinforcing fabric is 2 mm across.

3. The wound dressing of claim 1 wherein the thickness of the polyurethane in the area of the wound dressing where the polyurethane fills the interstices of said knitted reinforcing fabric is 0.01 mm.

4. The wound dressing of claim 1 where said knitted reinforcing fabric is formed from yarns having a diameter of 0.1 mm.

5. The wound dressing of claim 1 where said knitted reinforcing fabric is a material formed from Nylon 6-6 yarns.

6. The wound dressing of claim 1 further comprising a coating of pressure sensitive adhesive on one surface of said polyurethane encapsulated fabric layer.

7. The wound dressing of claim 1 where said polyurethane is the reaction product of
   (1) isophorone diisocyanate;
   (2) a macroglycol; and
   (3) a monomer containing hydroxyl and vinyl groups.

8. The wound dressing of claim 1 wherein said polyurethane containing said fabric embedded therein and encapsulated thereby has been cured by incorporation of a photosensitizer and exposure to ultraviolet light.

9. The wound dressing of claim 7 wherein said dressing is formed by:
   (1) reacting isophorone diisocyanate and said macroglycol together in the presence of a catalyst to form an isocyanate terminated prepolymer;
   (2) reacting said prepolymer with said monomer containing hydroxyl and vinyl groups to form an ultraviolet-curable, vinyl terminated polyurethane oligomer;
   (3) admixing said oligomer with the pharmacoactive agent to form an UV-curable homogeneous blend;
   (4) dipping said knitted reinforcing anisotropic fabric in said blend so that the blend coats the fibers of said fabric, fills the interstices of said fabric and encapsulates said fabric, forming an encapsulated fabric layer; and
   (5) curing the encapsulated fabric layer of step 4 by exposure to ultraviolet light to form said polyurethane encapsulated fabric layer.

10. The wound dressing of claim 9 further comprising a coating of a pressure sensitive adhesive on one surface of said polyurethane encapsulated fabric layer.

11. An anisotropic wound dressing comprising a biocompatable polyurethane fabric layer comprising:
    a biocompatible polyurethane; and
    a knitted reinforcing anisotropic fabric defining a network of interstices having a void area between the range of 0.5 mm to 4 mm across and formed from yarns having a diameter in the range of 0.025 to 0.203 mm adhered to said polyurethane;
    wherein the thickness of the polyurethane in the area of the wound dressing where the polyurethane fills the interstices of said knitted reinforcing fabric is 0.0254 mm or less.

12. The wound dressing of claim 11 where said void area of said knitted reinforcing fabric is 2 mm across.

13. The wound dressing of claim 11 wherein the thickness of the polyurethane in the area of the wound dressing where the polyurethane fills the interstices of said knitted reinforcing fabric is 0.01 mm.

14. The wound dressing of claim 11 where said knitted reinforcing fabric is formed from yarns having a diameter of 0.1 mm.

15. The wound dressing of claim 11 where said knitted reinforcing fabric is a material formed from Nylon 6-6 yarns.

16. The wound dressing of claim 11 further comprising a coating of pressure sensitive adhesive on one surface of said polyurethane fabric layer.

17. The wound dressing of claim 11 where said biocompatable polyurethane is the reaction product of:
    (1) isophorone diisocyanate;
    (2) a macroglycol; and
    (3) a monomer containing hydroxyl and vinyl groups.

18. The wound dressing of claim 11 wherein said biocompatable polyurethane has been cured by incorporation of a photosensitizer and exposure to ultraviolet light.

19. The wound dressing of claim 17 wherein said dressing is formed by:
    (1) reacting isophorone diisocyanate and said macroglycol together in the presence of a catalyst to form an isocyanate terminated prepolymer;
    (2) reacting said prepolymer with said monomer containing hydroxyl and vinyl groups to form an ultraviolet-curable, vinyl terminated polyurethane oligomer;

(3) admixing said oligomer with the pharmacoactive agent to form a UV-curable homogeneous blend;

(4) dipping said knitted reinforcing anisotropic fabric in said blend so that the blend coats the fibers of said fabric and fills the interstices of said fabric, forming a polyurethane fabric layer; and (5) curing the polyurethane fabric of step 4 by exposure to ultraviolet light to form said polyurethane fabric layer.

20. The wound dressing of claim 19 further comprising a coating of a pressure sensitive adhesive on one surface of said polyurethane fabric layer.

21. An anisotropic wound dressing comprising a biocompatable polyurethane encapsulated fabric layer comprising;

a biocompatible polyurethane; and a knitted reinforcing anisotropic fabric defining a network of interstices having a void area between the range of 0.5 mm to 4 mm across and formed from yarns having a diameter in the range of 0.025 to 0.203 mm embedded in and encapsulated by said polyurethane;

wherein the thickness of the polyurethane in the area of the wound dressing where the polyurethane fills the interstices of said knitted reinforcing fabric is 0.0254 mm or less.

22. The wound dressing of claim 21 where said void area of said knitted reinforcing fabric is 2 mm across.

23. The wound dressing of claim 21 wherein the thickness of the polyurethane in the area of the wound dressing where the polyurethane fills the interstices of said knitted reinforcing fabric is 0.01 mm.

24. The wound dressing of claim 21 where said knitted reinforcing fabric is formed from yarns having diameter of 0.1 mm.

25. The wound dressing of claim 21 where said knitted reinforcing fabric is a material formed from Nylon 6-6 yarns.

26. The wound dressing of claim 21 further comprising a coating of pressure sensitive adhesive on one surface of said polyurethane encapsulated fabric layer.

27. The wound dressing of claim 21 where said polyurethane is the reaction product of:

(1) isophorone diisocyanate;

(2) a macroglycol; and (3) a monomer containing hydroxyl and vinyl groups.

28. The wound dressing of claim 21 wherein said polyurethane containing said fabric embedded therein and encapsulated thereby has been cured by incorporation of a photosensitizer and exposure to ultraviolet light.

29. The wound dressing of claim 27 wherein said dressing is formed by:

(1) reacting isophorone diisocyanate and said macroglycol together in the presence of a catalyst to form an isocyanate terminated prepolymer;

(2) reacting said prepolymer with said monomer containing hydroxyl and vinyl groups to form an ultraviolet-curable, vinyl terminated polyurethane oligomer;

(3) admixing said oligomer with the pharmacoactive agent to form an UV-curable homogeneous blend;

(4) dipping said knitted reinforcing anisotropic fabric in said blend so that the blend coats the fibers of said fabric, fills the interstices of said fabric and encapsulates said fabric, forming an encapsulated fabric layer; and (5) curing the encapsulated fabric layer of step 4 by exposure to ultraviolet light to form said polyurethane encapsulated fabric layer.

30. The wound dressing of claim 29 further comprising a coating of a pressure sensitive adhesive on one surface of said polyurethane encapsulated fabric layer.

* * * * *